United States Patent
Baker et al.

(10) Patent No.: US 10,451,407 B2
(45) Date of Patent: Oct. 22, 2019

(54) SYSTEM AND METHOD OF ANALYZING A CURVED SURFACE

(71) Applicant: The Boeing Company, Huntington Beach, CA (US)

(72) Inventors: Anthony W. Baker, Gilbertsville, PA (US); Christopher Bellavia, St. Louis, MO (US)

(73) Assignee: THE BOEING COMPANY, Chicago, IL (US)

( * ) Notice: Subject to any disclaimer, the term of this patent is extended or adjusted under 35 U.S.C. 154(b) by 148 days.

(21) Appl. No.: 14/948,459

(22) Filed: Nov. 23, 2015

(65) Prior Publication Data

US 2017/0146462 A1 May 25, 2017

(51) Int. Cl.
| | | |
|---|---|---|
| *G06K 9/00* | (2006.01) | |
| *G06K 9/40* | (2006.01) | |
| *G06K 9/26* | (2006.01) | |
| *G01B 11/24* | (2006.01) | |
| *G01B 11/14* | (2006.01) | |
| *G06T 7/00* | (2017.01) | |
| *G01N 21/88* | (2006.01) | |
| *G01N 21/95* | (2006.01) | |

(52) U.S. Cl.
CPC ............ *G01B 11/24* (2013.01); *G01B 11/14* (2013.01); *G01N 21/8851* (2013.01); *G01N 21/9515* (2013.01); *G06T 7/001* (2013.01); *G01N 2021/8883* (2013.01); *G01N 2201/10* (2013.01); *G01N 2201/12* (2013.01); *G06T 2207/10028* (2013.01); *G06T 2207/20056* (2013.01)

(58) Field of Classification Search
CPC ............... G01N 21/95; G01N 2201/10; G01N 2201/12; G01B 11/14; G01B 11/24; G06T 7/0004; G06T 7/604; G06T 2207/10028; G06T 2207/20056
USPC ................................ 382/154, 141, 275, 322
See application file for complete search history.

(56) References Cited

U.S. PATENT DOCUMENTS

| | | | | |
|---|---|---|---|---|
| 4,949,281 A | * | 8/1990 | Hillenbrand | ............ B41B 19/02 345/442 |
| 4,979,224 A | * | 12/1990 | Maiocco | ............ G05B 19/4207 382/154 |
| 5,311,600 A | * | 5/1994 | Aghajan | ............... G06K 9/4604 382/156 |
| 5,973,777 A | * | 10/1999 | Nomoto | ................. G01N 21/88 356/237.5 |
| 6,363,163 B1 | * | 3/2002 | Xu | ............................. G06T 5/50 382/130 |
| 6,611,617 B1 | * | 8/2003 | Crampton | .......... G01B 11/2518 356/614 |
| 7,162,073 B1 | * | 1/2007 | Akgul | ................ G01N 21/8851 348/125 |

(Continued)

*Primary Examiner* — Kathleen Y Dulaney
(74) *Attorney, Agent, or Firm* — Armstrong Teasdale LLP

(57) ABSTRACT

A method of analyzing a curved surface is provided. The method includes obtaining a first data point set including data points representative of a distance between points along the curved surface and a reference axis, determining outlier data points in the first data point set, extracting the outlier data points from the first data point set, thereby defining a second data point set. The method also includes determining a fitted curve for the second data point set, wherein the fitted curve defines an approximate true curve of the curved surface.

12 Claims, 3 Drawing Sheets

(56) References Cited

U.S. PATENT DOCUMENTS

| | | | | |
|---|---|---|---|---|
| 7,171,054 B2* | 1/2007 | Fiete | ............... | G02B 7/36 358/1.5 |
| 7,256,899 B1* | 8/2007 | Faul | ............... | G01B 11/2522 356/623 |
| 7,616,800 B2* | 11/2009 | Paik | ............... | G06K 9/00214 382/131 |
| 7,616,807 B2* | 11/2009 | Zhang | ............... | G06T 7/246 345/419 |
| 7,620,265 B1* | 11/2009 | Wolff | ............... | G06T 5/50 382/254 |
| 7,742,635 B2* | 6/2010 | Rohaly | ............... | G06T 7/593 382/106 |
| 7,826,646 B2* | 11/2010 | Pavlovskaia | ............... | A61C 7/002 382/128 |
| 7,925,075 B2* | 4/2011 | Jia | ............... | G01B 21/20 382/145 |
| 7,974,722 B2* | 7/2011 | Boyl-Davis | ............... | G06F 17/50 264/515 |
| 8,233,742 B2 | 7/2012 | Masuda | | |
| 8,355,601 B2* | 1/2013 | Ding | ............... | H04N 9/3182 348/189 |
| 8,849,620 B2* | 9/2014 | Regan | ............... | G06F 17/50 703/1 |
| 8,867,806 B2* | 10/2014 | Hibbard | ............... | G06T 17/30 382/128 |
| 9,652,043 B2* | 5/2017 | Kang | ............... | G06F 3/017 |
| 2003/0053696 A1* | 3/2003 | Schmidt | ............... | G06K 9/4604 382/199 |
| 2003/0095710 A1* | 5/2003 | Tessadro | ............... | G06T 7/12 382/199 |
| 2005/0147283 A1* | 7/2005 | Dwyer | ............... | G06T 7/0012 382/128 |
| 2006/0098893 A1* | 5/2006 | Kondo | ............... | G06K 9/4609 382/266 |
| 2007/0171396 A1* | 7/2007 | Harris | ............... | G01S 7/493 356/28 |
| 2008/0013822 A1* | 1/2008 | Pai | ............... | G01N 21/9501 382/145 |
| 2008/0205747 A1* | 8/2008 | Kuchii | ............... | G06T 5/20 382/149 |
| 2009/0022393 A1* | 1/2009 | Bar-Zohar | ............... | G06T 7/593 382/154 |
| 2009/0046896 A1* | 2/2009 | Yamaguchi | ............... | G06K 9/4604 382/106 |
| 2009/0310867 A1* | 12/2009 | Matei | ............... | G06T 7/11 382/195 |
| 2011/0135190 A1* | 6/2011 | Maad | ............... | A61B 6/0407 382/154 |
| 2013/0051658 A1* | 2/2013 | Hwang | ............... | G06K 9/00201 382/154 |
| 2013/0336575 A1* | 12/2013 | Dalla-Torre | ............... | G06T 7/001 382/149 |
| 2014/0133749 A1* | 5/2014 | Kuo | ............... | G06T 7/90 382/167 |
| 2014/0133750 A1* | 5/2014 | Fredlund | ............... | G06T 5/009 382/167 |
| 2015/0138310 A1* | 5/2015 | Fan | ............... | G06K 9/00201 348/36 |
| 2015/0213606 A1 | 7/2015 | Akopyan et al. | | |
| 2015/0332451 A1* | 11/2015 | Amzaleg | ............... | G06T 7/001 382/149 |
| 2016/0014395 A1* | 1/2016 | Murray | ............... | G01S 17/89 348/42 |
| 2016/0103443 A1* | 4/2016 | Bryll | ............... | G05B 19/21 700/114 |
| 2016/0146595 A1* | 5/2016 | Boufounos | ............... | G01S 17/89 348/47 |
| 2016/0196666 A1* | 7/2016 | Venkatraghavan | ...... | G06T 7/254 382/130 |
| 2016/0379341 A1* | 12/2016 | Domanski | ............... | H04N 13/111 382/154 |

\* cited by examiner

SYSTEM AND METHOD OF ANALYZING A CURVED SURFACE

BACKGROUND

The field of the present disclosure relates generally to analytical systems and, more specifically, to systems and methods of determining anomalies in a curved surface.

Objects are often inspected to facilitate maintaining a desired level of quality and/or consistency during fabrication thereof, or to detect damage during the service life of the object. Many inspections are either performed manually by a trained operator or using one or more sensor collection techniques. For example, sensor collection techniques such as light detection and ranging (LiDAR), stereo imagery, time-of-flight cameras, and laser line-scan sensors provide data on the surface of the object being scanned. However, it is common for anomalies on the surface of the object to be detected from either anomalous readings from the sensor, or from actual defects in the surface being scanned. Determining the presence of anomalies on the surface of the object is further complicated when the surface is curved, or otherwise arbitrarily shaped, which further increases the difficulty in distinguishing defects in the surface from the actual shape of the object.

BRIEF DESCRIPTION

In one aspect, a method of analyzing a curved surface is provided. The method includes obtaining a first data point set including data points representative of a distance between points along the curved surface and a reference axis, determining outlier data points in the first data point set, extracting the outlier data points from the first data point set, thereby defining a second data point set. The method also includes determining a fitted curve for the second data point set, wherein the fitted curve defines an approximate true curve of the curved surface.

In another aspect, a system for use in analyzing a curved surface is provided. The system includes a scanning device that obtains a first data point set including data points representative of a distance between points along the curved surface and a reference axis, and a computing device coupled in communication with the scanning device. The computing device determines outlier data points in the first data point set, extracts the outlier data points from the first data point set, thereby defining a second data point set, and determines a fitted curve for the second data point set, wherein the fitted curve defines an approximate true curve of the curved surface.

In yet another aspect, a non-transitory computer-readable media having computer-executable instructions embodied thereon for use in analyzing a curved surface is provided. When executed by a computing device, the computer-executable instructions cause the computing device to determine outlier data points in a first data point set, wherein the first data point set includes data points representative of a distance between points along the curved surface and a reference axis. The computer-executable instructions further cause the computing device to extract the outlier data points from the first data point set, thereby defining a second data point set, and determine a fitted curve for the second data point set, wherein the fitted curve defines an approximate true curve of the curved surface.

DETAILED DESCRIPTION

The implementations described herein relate to systems and methods of analyzing a curved surface. More specifically, the systems and methods described herein facilitate determining anomalies in a curved surface by obtaining either a two-dimensional or three-dimensional representation of a real world object from data point set representative of height values for the surface. Outlier data points in the data point set are then determined and extracted to facilitate approximating a true curve of the curved surface, rather than normalizing the data points to determine variations in a theoretical flat surface. As such, the approximated true curve of the curved surface can then be compared to the data points in the data point set to determine anomalies in the curved surface in a more efficient and less time consuming manner.

Figure 1:
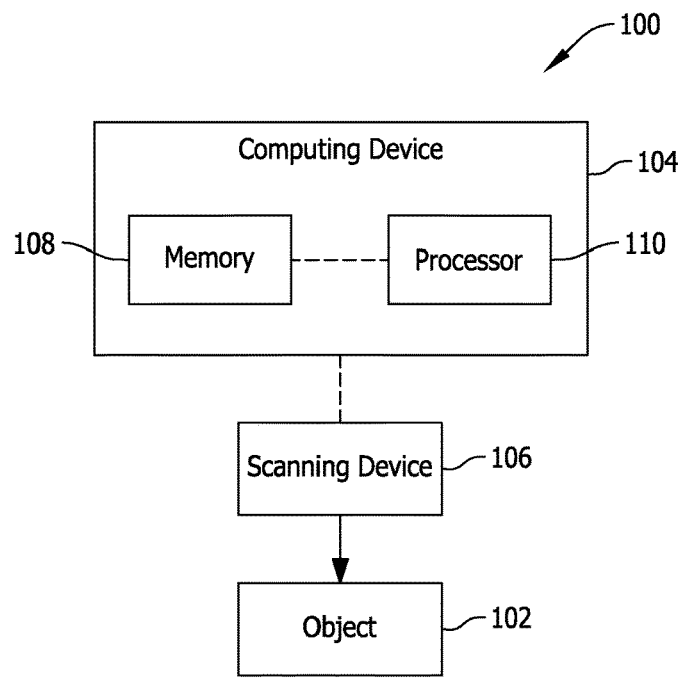
FIG. 1 is a block diagram of an exemplary system for use in analyzing a curved surface.

FIG. 1 is a block diagram of an exemplary system 100 for use in analyzing a curved surface. More specifically, system 100 facilitates analyzing an object 102 having a curved surface. As used herein, "curved surface" refers to a surface having at least a portion that is non-planar. In the exemplary implementation, system 100 includes a computing device 104 coupled in communication with a scanning device 106. Scanning device 106 is any device capable of obtaining vertical displacement values of the curved surface, for further evaluation relative to a reference axis and/or reference plane, as will be described in more detail below. Exemplary scanning devices include, but are not limited to, a light detection and ranging (LiDAR) device, a stereo imagery device, a time-of-flight camera, and a laser line-scanning device.

Computing device 104 includes a memory 108 and a processor 110, comprising hardware and software, coupled to memory 108 for executing programmed instructions. Processor 110 may include one or more processing units (e.g., in a multi-core configuration) and/or include a cryptographic accelerator (not shown). Computing device 104 is programmable to perform one or more operations described herein by programming memory 108 and/or processor 110. For example, processor 110 may be programmed by encoding an operation as executable instructions and providing the executable instructions in memory 108.

Processor 110 may include, but is not limited to, a general purpose central processing unit (CPU), a microcontroller, a reduced instruction set computer (RISC) processor, an open media application platform (OMAP), an application specific integrated circuit (ASIC), a programmable logic circuit (PLC), and/or any other circuit or processor capable of executing the functions described herein. The methods described herein may be encoded as executable instructions embodied in a computer-readable medium including, without limitation, a storage device and/or a memory device. Such instructions, when executed by processor 110, cause processor 110 to perform at least a portion of the functions described herein. The above examples are exemplary only, and thus are not intended to limit in any way the definition and/or meaning of the term processor.

Memory 108 is one or more devices that enable information such as executable instructions and/or other data to be stored and retrieved. Memory 108 may include one or more computer-readable media, such as, without limitation, dynamic random access memory (DRAM), synchronous dynamic random access memory (SDRAM), static random access memory (SRAM), a solid state disk, and/or a hard disk. Memory 108 may be configured to store, without limitation, executable instructions, operating systems, applications, resources, installation scripts and/or any other type of data suitable for use with the methods and systems described herein.

Instructions for operating systems and applications are located in a functional form on non-transitory memory 108 for execution by processor 110 to perform one or more of the processes described herein. These instructions in the different implementations may be embodied on different physical or tangible computer-readable media, such as memory 108 or another memory, such as a computer-readable media (not shown), which may include, without limitation, a flash drive and/or thumb drive. Further, instructions may be located in a functional form on non-transitory computer-readable media, which may include, without limitation, smart-media (SM) memory, compact flash (CF) memory, secure digital (SD) memory, memory stick (MS) memory, multimedia card (MMC) memory, embedded-multimedia card (e-MMC), and micro-drive memory. The computer-readable media may be selectively insertable and/or removable from computing device 104 to permit access and/or execution by processor 110. In an alternative implementation, the computer-readable media is not removable.

In operation, scanning device 106 obtains a first data point set including data points representative of a distance between points along the curved surface of object 102 and a reference axis. The first data point set is transmitted to computing device 104, and computing device 104 determines outlier data points in the first data point set, extracts the outlier data points from the first data point set, thereby defining a second data point set, and determines a fitted curve for the second data point set. The fitted curve defines an approximated true curve of the curved surface, and the approximated true curve can be used to determine anomalies on object 102, as will be explained in more detail below.

Figure 2:
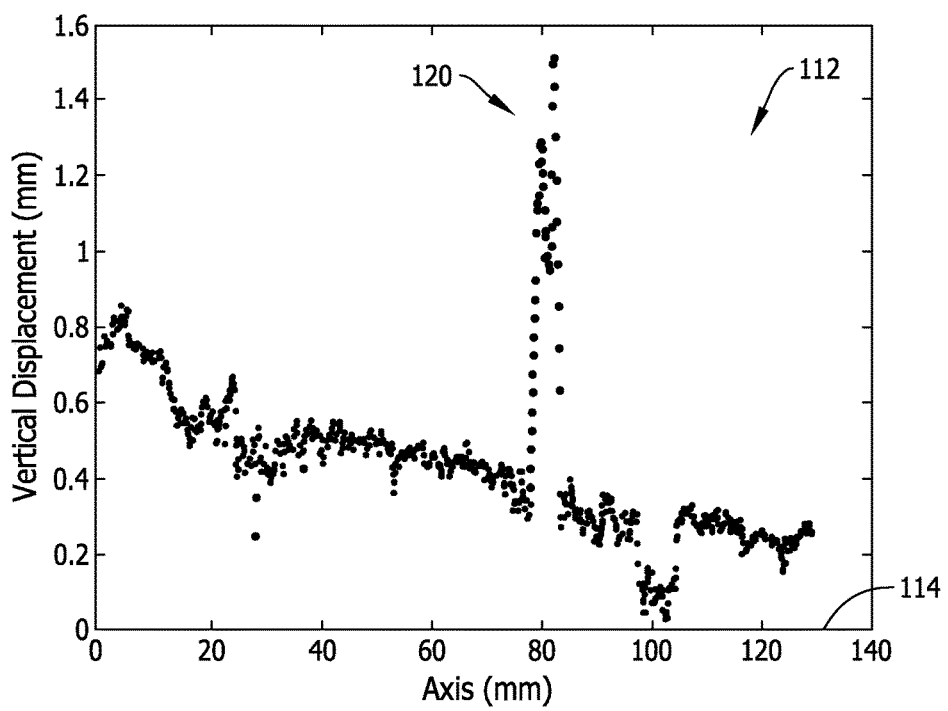
FIG. 2 is an exemplary plot of a first data point set representative of a vertical displacement along the curved surface of an object shown in FIG. 1 relative to a reference axis.
Figure 3:
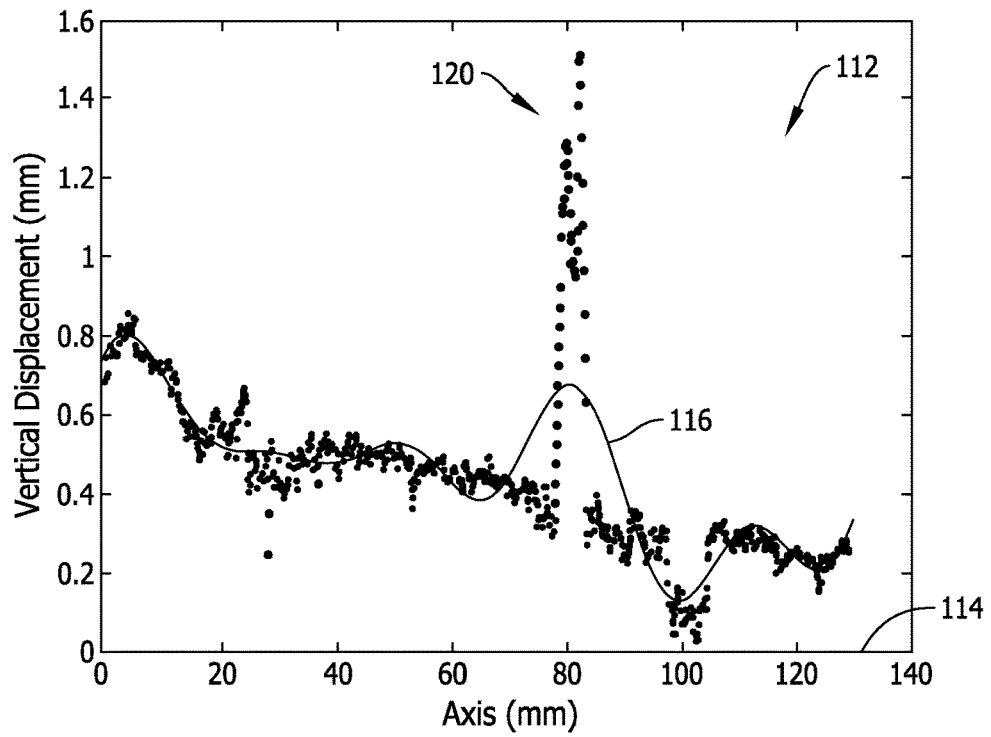
FIG. 3 is an exemplary plot of the first data point set shown in FIG. 2 having a first fitted curve plotted thereon.
Figure 4:
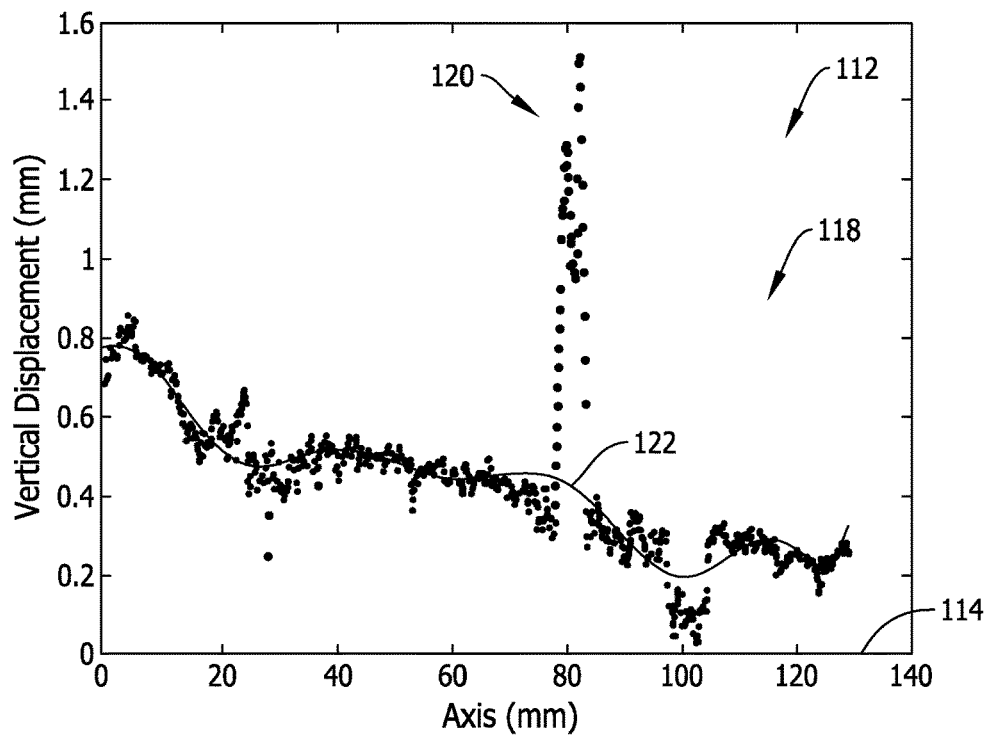
FIG. 4 is an exemplary plot of a second data point set having a second fitted curved plotted thereon.

FIG. 2 is an exemplary plot of a first data point set 112 representative of a vertical displacement along the curved surface of object 102 (shown in FIG. 1) relative to a reference axis 114, FIG. 3 is an exemplary plot of first data point set 112 having an initial, first fitted curve 116 plotted thereon, and FIG. 4 is an exemplary plot of a second data point set 118 having a second fitted curved plotted thereon. In the exemplary implementation, and as described above, scanning device 106 scans object 102 to obtain first data point set 112 representing vertical displacement values relative to reference axis 114 along an example span of the curved surface of object 102. For example, reference axis 114 is an axis in a standard coordinate system such that a variable vertical displacement is defined between data points in first data point set 112 and reference axis 114. As shown in FIG. 2, a potential anomaly 120 is detected at about the exemplary 80 mm mark along reference axis 114. Without extracting the data points representing potential anomaly 120, referring to FIG. 3, first fitted curve 116 was fit to the data points in first data point set 112 to approximate a true curve of the curved surface. First fitted curve 116 was fit using the Levenberg-Marquardt algorithm, also known as damped least squares, to fit the model using a fifth order Fourier series approximation. The damped least squares can also be used to fit an $n^{th}$ degree polynomial approximation, wherein the algorithm determines the n coefficients of the polynomial. As shown in FIG. 3, first fitted curve 116 is perturbed by potential anomaly 120 at about the 80 mm mark along reference axis 114. In an alternative implementation, the computations used in the methodologies described herein can be performed manually.

Referring to FIG. 4, data points in first data point set 112 corresponding to extreme outliers in first data point set 112 are removed therefrom to define a second data point set 118. More specifically, in the exemplary implementation, computing device 104 determines residuals (i.e., differences) for the data points in first data point set 112 relative to first fitted curve 116. Computing device 104 then determines a standard deviation for the residuals, and defines the outlier data points based on the standard deviation for the residuals. For example, in one implementation, any data points in first data point set 112 outside of two standard deviations for the residuals is defined as an outlier data point. Computing device 104 removes the outlier data points from first data point set 112 to define second data point set 118, and the model is refit to define a second fitted curve 122 from the data points in second data point set 118. Alternatively, the process of determining and removing outlier data points can be repeated more than once to provide a more accurate determination of the approximate true curve of the curved surface of object 102. Moreover, the number of iterations can be dynamically determined using a stopping time algorithm based on the number of outlier data point discarded at each iteration.

In one implementation, computing device 104 determines a plurality of Fourier transforms for data points in second data point set 118, and plots second fitted curve 122 based on the plurality of Fourier transforms. As such, a smooth approximation for the curved surface of object 102 is defined in the form of second fitted curve 122, and second fitted curve 122 can be used to determine the presence and location of anomalies on object 102. Alternatively, computing device 104 determines a third or higher degree polynomial representation for data points in the data point set, and plots second fitted curve 122 based on the polynomial representation. Computing device 104 then compares second fitted curve 122 to the data points in first data point set 112 to determine anomalies in the curved surface. The determination of which data points in first data point set 112 are anomalies on object 102 can be based on any methodology that enables the systems and methods to function as described herein. For example, in one implementation, computing device 104 determines data points in first data point set 112 having a vertical displacement relative to second fitted curve 122 greater than a predetermined threshold. The data points having the vertical displacement greater than the predetermined threshold are either defined as anomalous portions of object 102, or are designated for future inspection.

Figure 5:
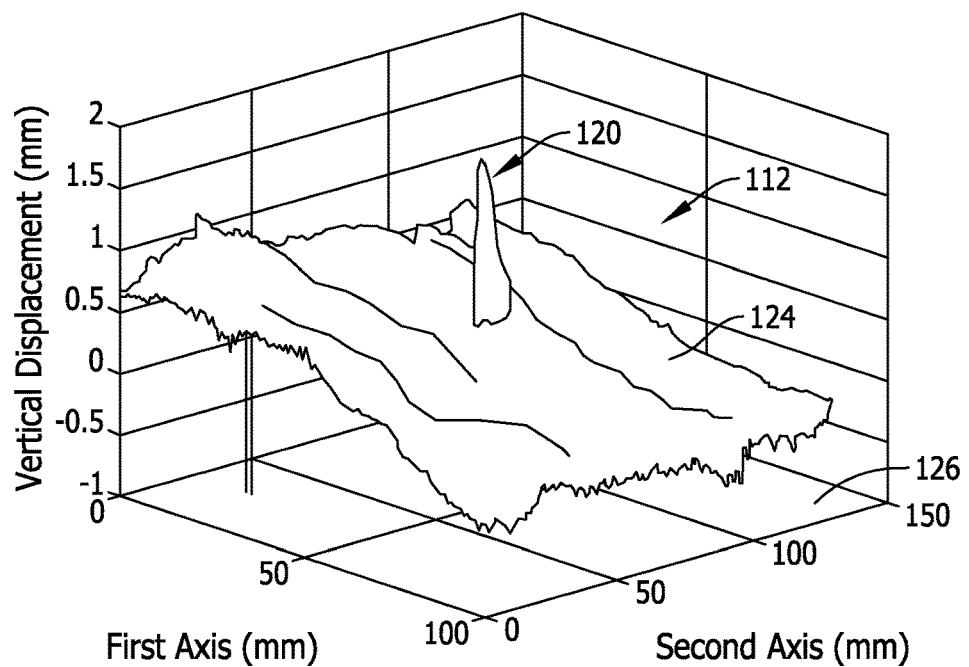
FIG. 5 is an exemplary plot of a first fitted surface of the first data point set representative of a vertical displacement along the curved surface relative to a reference plane.
Figure 6:
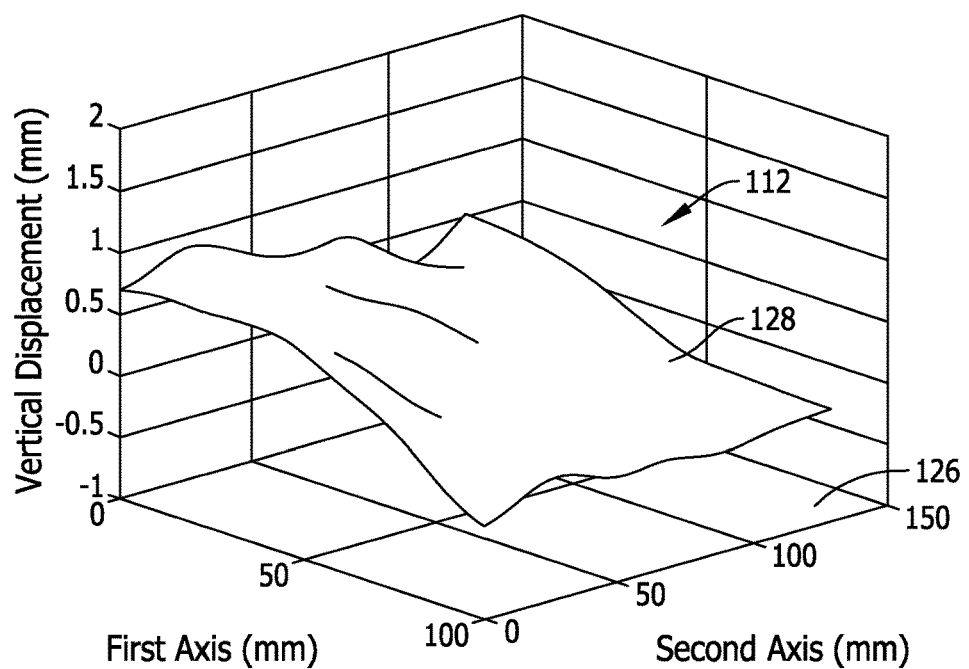
FIG. 6 is an exemplary plot of a second fitted surface for the first data point set shown in FIG. 5.

FIG. 5 is an exemplary first fitted surface 124 of first data point set 112 representative of a vertical displacement along the curved surface of object 102 (shown in FIG. 1) relative to a reference plane 126, and FIG. 6 is an exemplary plot of a second fitted surface 128 for first data point set 112. In the exemplary implementation, potential anomaly 120 in the curved surface is detected relative to reference plane 126. In one implementation, reference plane 126 is a plane in a standard coordinate system. Similar to the method articulated in FIGS. 2-4, computing device 104 (shown in FIG. 1) uses a Fast Fourier Transform algorithm to determine the plurality of Fourier transforms for data points in first data point set 112. More specifically, the Fast Fourier Transform algorithm determines the Discrete Fourier Transform of n points in loglinear time (e.g., O(nlog(n))). Computing device 104 then plots first fitted surface 124 based on the plurality of Fourier transforms. Alternatively, a least squares curve fitting of polynomial equation can be executed on a graphical processing unit (GPU) (not shown).

More specifically, in one implementation, a two-dimensional array of discrete points representing a surface or image is input into a surface fitting function. The function creates a buffer on the boundaries of the matrix and computes the Fast Fourier Transform. The resulting frequency domain terms are truncated using a mask generated to capture a defined amount of frequency information. Computing device 104 then determines the inverse Fast Fourier Transform from the truncated frequency values. This mask facilitates removing higher order Fourier coefficients such that first fitted surface 124 only contains the low-frequency, smooth terms.

First fitted surface 124 can be used to determine the presence and location of anomalies on object 102. More specifically, in the exemplary implementation, computing device 104 determines residuals (i.e., differences) for the data points in first data point set 112 relative to first fitted surface 124. Computing device 104 then determines a standard deviation for the residuals, and defines the outlier data points based on the standard deviation for the residuals. For example, in one implementation, any data points in first data point set 112 outside of two standard deviations for the residuals is defined as an outlier data point. Unlike the method articulated in FIGS. 2-4, computing device 104 does not remove the outlier data points from first data point set 112 such that the matrix size remains the same size for further computations. Instead, in the exemplary implementation, computing device 104 uses a box filter, or averaging filter, to determine a convolution with the data points, which provides localized neighborhood mean values. Computing device 104 then replaces the outlier data points with the localized neighborhood mean values.

Referring to FIG. 6, second fitted surface 128 is plotted using the same Fast Fourier Transform computation, masking, and inverse Fast Fourier Transform computation steps as first fitted surface. Computing device 104 then compares second fitted surface 128 to the data points in first data point set 112 to determine anomalies in the curved surface. The determination of which data points in first data point set 112 are anomalies on object 102 can be based on any methodology that enables the systems and methods to function as described herein. For example, in one implementation, computing device 104 determines data points in first data point set 112 having a vertical displacement relative to second fitted surface 128 greater than a predetermined threshold. The data points having the vertical displacement greater than the predetermined threshold are either defined as anomalous portions of object 102, or are designated for future inspection.

In some implementations, there are several parameters used in the algorithms for determining the fitted curves and fitted surfaces that are taken into consideration. One parameter is the smoothness or curvature of the fitted curves and fitted surfaces. For example, the curvature of the fitted curves and fitted surfaces is represented by the number of terms in the polynomial expansion or the number of terms in the Fourier expansion. If the correct number of terms for the problem is underestimated, a high number of false-positives in the detection of anomalies will be determined. If the number of terms for the problem is overestimated, the furthest outliers will be close to the fitted curve/surface, and will be not considered an outlier data point. The object being analyzed will typically have a natural maximum curvature that can be used to determine the correct answer for the problem. An alternate method for controlling curvature not outlined above is to control the magnitude of the Fourier coefficients for the terms at the end of the expansion.

Moreover, the statistical analysis provides the associated threshold for the initial outlier data point identification. In the exemplary implementation, a $2\sigma$ threshold is used. By modifying the threshold, the derived comparison surface is also modified. The identification threshold is also a function of the noise level of the sensor. If the noise level of the sensor is large, the threshold for identifying anomalies will be large as well. As such, the algorithm can be modified to provide a smoothing filter prior to curve/surface fitting step.

This written description uses examples to disclose various implementations, including the best mode, and also to enable any person skilled in the art to practice the various implementations, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of analyzing a curved surface of an object, said method implemented by a computing device including at least one processor in communication with at least one memory device, said method comprising:

scanning, by a light detection and ranging (LiDAR) device, the object to obtain a first data point set representative of vertical displacements of points along the curved surface from a reference axis along which the LiDAR device operates, wherein the reference axis is an axis in a Cartesian coordinate system such that the vertical displacements vary along the curved surface, and wherein scanning the object to obtain the first data point set further comprises scanning the object to obtain a three-dimensional point cloud representative of a distance between points along the curved surface and a reference plane;

determining, by the computing device, outlier data points in the first data point set based on a noise level of the LiDAR device, wherein determining the outlier data points comprises:

determining, for the first data point set, an initial fitted curve approximating a true curve of the curved surface, wherein determining the initial fitted curve comprises:

applying a surface fitting function to a two-dimensional array of data points of the first data point set to create a buffer on boundaries of the array and compute a Fast Fourier transform;

truncating frequency domain values resulting from the Fast Fourier transform using an elliptical mask, wherein the elliptical mask facilitates removing higher order Fourier coefficients such that the reference plane contains only low-frequency, smooth terms;

determining an inverse Fast Fourier transform from the truncated frequency domain values; and generating a three-dimensional first fitted surface of the object based on the determined inverse Fast Fourier transform;

computing respective differences between each data point of the first data point set and the initial fitted curve;

determining a standard deviation of the respective differences; and identifying the outlier data points among the first data point set as data points corresponding to respective differences greater than the standard deviation;

extracting, by the computing device, the outlier data points from the first data point set, leaving a second data point set;

determining, by the computing device using a plurality of Fourier transform for the second data point set, a second fitted curve for the second data point set, wherein the second fitted curve approximates the true curve of the curved surface; and identifying, by the computing device, one or more anomalous portions of the object based on the second fitted curve and the second data point set, the one or more anomalous portions indicative of a potential defect in the curved surface of the object.

2. The method in accordance with claim 1 further comprising comparing the second fitted curve to data points of the first data point set to determine anomalies in the curved surface.

3. The method in accordance with claim 1, wherein determining the second fitted curve comprises:

determining a plurality of Fourier transforms for the second data point set; and plotting the second fitted curve based on the plurality of Fourier transforms for the second data point set.

4. The method in accordance with claim 1, wherein extracting the outlier data points from the first data point set further comprises:

determining, using an averaging filter, a convolution of the data points from the first data point set to generate localized neighborhood mean values; and replacing the outlier data points with the localized neighborhood mean values.

5. A system for use in analyzing a curved surface of an object, said system comprising:

a light detection and ranging (LiDAR) device that scans the curved surface and obtains a first data point set representative of vertical displacements of points along the curved surface from a reference axis along which the LiDAR device operates, wherein the reference axis is an axis in a Cartesian coordinate system such that the vertical displacements vary along the curved surface, and wherein to obtain the first data point set, said scanning device obtains a three-dimensional point cloud representative of a distance between points along the curved surface and a reference plane; and a computing device coupled in communication with said scanning device, wherein said computing device is configured to:

determine, for the first data point set, an initial fitted curve approximating a true curve of the curved surface, wherein to determine, for the first data point set, the initial fitted curve, said computing device further:

applies a surface fitting function to a two-dimensional array of the data points of the first data point set to create a buffer on boundaries of the array and compute a Fast Fourier transform;

truncates frequency domain values resulting from the Fast Fourier transform using an elliptical mask, wherein the elliptical mask facilitates removing higher order Fourier coefficients such that the reference plane contains only low-frequency, smooth terms;

determines an inverse Fast Fourier transform from the truncated frequency domain values; and generates a three-dimensional first fitted surface of the object based on the determined inverse Fast Fourier transform;

compute respective differences between each data point of the first data point set and the initial fitted curve;

determine a standard deviation of the respective differences;

identify outlier data points among the first data point set as data points corresponding to respective differences greater than the standard deviation and based on a noise level of said scanning device;

extract the outlier data points from the first data point set, leaving a second data point set;

determine a second fitted curve for the second data point set using a plurality of Fourier transforms for the second data point set, wherein the second fitted curve approximates the true curve of the curved surface; and identify one or more anomalous portions of the object based on the second fitted curve and the second data point set, the one or more anomalous portions indicative of a potential defect in the curved surface of the object.

6. The system in accordance with claim 5, wherein said computing device is further configured to compare the second fitted curve to data points of the first data point set to determine anomalies in the curved surface.

7. The system in accordance with claim 5, wherein said computing device is further configured to:

determine a plurality of Fourier transforms for data points in the second data point set; and plot the second fitted curve based on the plurality of Fourier transforms for the second data point set.

8. The system in accordance with claim 5, to extract the outlier data points from the first data point set, said computing device further:

determines, using an averaging filter, a convolution of the data points from the first data point set to generate localized neighborhood mean values; and replaces the outlier data points with the localized neighborhood mean values.

9. A non-transitory computer-readable storage device having computer-executable instructions embodied thereon for use in analyzing a curved surface of an object, wherein, when executed by a computing device, the computer-executable instructions cause the computing device to:

receive, from a light detection and ranging (LiDAR) device, a first data point set based on one or more scans of the object by the LiDAR device, wherein the first data point set includes vertical displacements of points along the curved surface from a reference axis along which the LiDAR device operates, wherein the reference axis is an axis in a Cartesian coordinate system such that the vertical displacements vary along the curved surface, wherein to receive the first data point set, the instructions further cause the computing device to receive the first data point set including a three-dimensional point cloud representative of a distance between points along the curved surface and a reference plane;
determine outlier data points in the first data point set based on a noise level of the LiDAR device, wherein to determine the outlier data points the computer-executable instructions cause the computing device to:
  determine, for the first data point set, an initial fitted curve approximating a true curve of the curved surface, wherein to determine, for the first data point set, the initial fitted curve, the instructions further cause the computing device to:
    apply a surface fitting function to a two-dimensional array of the data points of the first data point set to create a buffer on boundaries of the array and compute a Fast Fourier transform;
    truncate frequency domain values resulting from the Fast Fourier transform using an elliptical mask, wherein the elliptical mask facilitates removing higher order Fourier coefficients such that the reference plane contains only low-frequency, smooth terms;
    determine an inverse Fast Fourier transform from the truncated frequency domain values; and
    generate a three-dimensional first fitted surface of the object based on the determined inverse Fast Fourier transform;
  compute respective differences between each data point of the first data point set and the initial fitted curve;
  determine a standard deviation of the respective differences; and
  identify the outlier data points among the first data point set as data points corresponding to respective distances greater than the standard deviation;
extract the outlier data points from the first data point set, leaving a second data point set;
determine a second fitted curve for the second data point set using a plurality of Fourier transforms for the second data point set, wherein the second fitted curve approximates the true curve of the curved surface; and
identify one or more anomalous portions of the object based on the second fitted curve and the second data point set, the one or more anomalous portions indicative of a potential defect in the curved surface of the object.

10. The non-transitory computer-readable storage device in accordance with claim 9 further comprising computer-executable instructions that cause the computing device to compare the true curve to data points of the first data point set to determine anomalies in the curved surface.

11. The non-transitory computer-readable storage device in accordance with claim 9 further comprising computer-executable instructions that cause the computing device to:
  determine a plurality of Fourier transforms for data points in the second data point set; and
  plot the second fitted curve based on the plurality of Fourier transforms for the second data point set.

12. The non-transitory computer-readable storage device in accordance with claim 9, wherein to extract the outlier data points from the first data point set, further comprising computer-executable instructions that cause the computing device to:
  determine, using an averaging filter, a convolution of the data points from the first data point set to generate localized neighborhood mean values; and
  replace the outlier data points with the localized neighborhood mean values.

* * * * *